(12) United States Patent
Kokish et al.

(10) Patent No.: US 6,544,221 B1
(45) Date of Patent: Apr. 8, 2003

(54) BALLOON DESIGNS FOR DRUG DELIVERY

(75) Inventors: Arkady Kokish, Los Gatos, CA (US);
Charlie W. Snyder, San Francisco, CA (US)

(73) Assignee: Advanced Cardiovascular Systems, Inc., Santa Clara, CA (US)

( * ) Notice: Subject to any disclaimer, the term of this patent is extended or adjusted under 35 U.S.C. 154(b) by 161 days.

(21) Appl. No.: 09/651,427

(22) Filed: Aug. 30, 2000

(51) Int. Cl.⁷ .............................................. A61M 29/00
(52) U.S. Cl. .................. 604/103.01; 604/523; 604/509; 623/1.11
(58) Field of Search ........................ 604/103.01, 96.01, 604/523, 508, 101.01, 101.05, 103.02, 103.06, 103.07, 509; 606/194, 191, 192; 623/1.11

(56) References Cited

U.S. PATENT DOCUMENTS

| | | | |
|---|---|---|---|
| 4,994,033 A | * 2/1991 | Shockey et al. | 604/101.02 |
| 5,049,132 A | * 9/1991 | Shaffer et al. | 604/101.02 |
| 5,213,576 A | * 5/1993 | Abiuso et al. | 604/101.02 |
| 5,286,254 A | * 2/1994 | Shapland et al. | 604/103.01 |
| 5,318,531 A | * 6/1994 | Leone | 604/103.01 |
| 5,514,092 A | * 5/1996 | Forman et al. | 604/101.03 |
| 5,569,184 A | * 10/1996 | Crocker et al. | 604/103.01 |
| 5,611,775 A | 3/1997 | Machold et al. | 604/53 |
| 5,681,281 A | * 10/1997 | Vigil et al. | 604/103.01 |
| 5,823,996 A | * 10/1998 | Sparks | 604/103.01 |
| 5,843,116 A | 12/1998 | Crocker et al. | 606/192 |
| 5,866,561 A | * 2/1999 | Ungs | 514/182 |
| 6,152,141 A | * 11/2000 | Stevens et al. | 128/898 |
| 6,210,392 B1 | * 4/2001 | Vigil et al. | 604/103.02 |

* cited by examiner

Primary Examiner—Brian L. Casler
Assistant Examiner—Cris Rodriguez
(74) Attorney, Agent, or Firm—Fulwider Patton Lee & Utecht, LLP

(57) ABSTRACT

The invention is directed to an inflatable member for delivery of therapeutic agents to a desired site within a patient's body, in particular, balloons for use with balloon catheters and stent delivery systems; balloon catheters and stent delivery systems including the same; and methods for making and using the same. The inflatable member of the present invention includes an outer and an inner layer and an outer chamber therebetween for housing the therapeutic agent. The outer layer includes apertures for releasing the therapeutic agent to the desired site. Optionally, the inner layer may also include perforations.

12 Claims, 4 Drawing Sheets

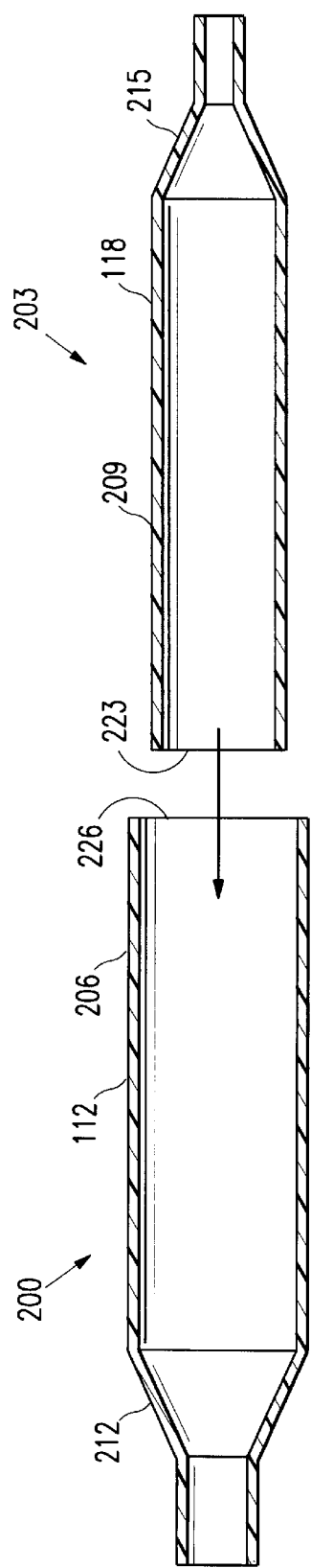
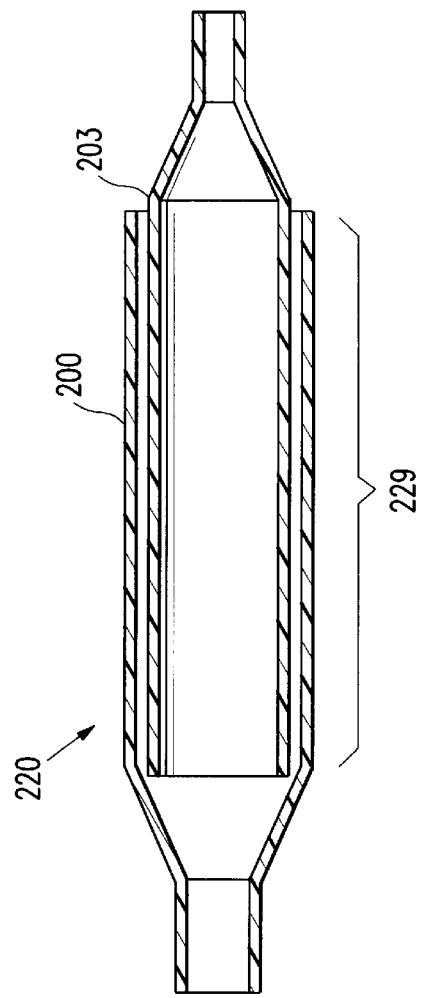
FIG. 6A
FIG. 6B

BALLOON DESIGNS FOR DRUG DELIVERY

FIELD OF INVENTION

The invention relates to the field of intravascular delivery systems, and more particularly to balloon designs for drug delivery.

BACKGROUND OF THE INVENTION

In percutaneous transluminal coronary angioplasty (PTCA) procedures, a guiding catheter is advanced until the distal tip of the guiding catheter is seated in the ostium of a desired coronary artery. A guide wire, positioned within an inner lumen of an dilatation catheter, is first advanced out of the distal end of the guiding catheter into the patient's coronary artery until the distal end of the guide wire crosses a lesion to be dilated. Then the dilatation catheter having an inflatable balloon on the distal portion thereof is advanced into the patient's coronary anatomy, over the previously introduced guide wire, until the balloon of the dilatation catheter is properly positioned across the lesion. Once properly positioned, the dilatation balloon is inflated with liquid one or more times to a predetermined size at relatively high pressures (e.g. greater than 8 atmospheres) so that the stenosis is compressed against the arterial wall and the wall expanded to open up the passageway. Generally, the inflated diameter of the balloon is approximately the same diameter as the native diameter of the body lumen being dilated so as to complete the dilatation but not overexpand the artery wall. After the balloon is finally deflated, blood flow resumes through the dilated artery and the dilatation catheter can be removed therefrom.

After angioplasty procedures, restenosis may form in the artery at the original stenotic site, necessitating either another angioplasty procedure, or some other method of repairing or strengthening the dilated area. To reduce the restenosis rate and to strengthen the dilated area, physicians frequently implant an intravascular prosthesis, generally called a stent, inside the artery at the site of the lesion. Stents may also be used to repair vessels having an intimal flap or dissection or to generally strengthen a weakened section of a vessel. Stents are usually delivered to a desired location within a coronary artery in a contracted condition on a balloon of a catheter which is similar in many respects to a balloon angioplasty catheter, and expanded to a larger diameter by expansion of the balloon. The balloon is deflated to remove the catheter and the stent left in place within the artery at the site of the dilated lesion.

At times during the angioplasty procedure or the stent delivery, it is desirable to deliver therapeutic agents specifically in the stenoic regions of the patient's coronary under treatment.

Therefore, what has been needed are balloons with improved design for the specific delivery of therapeutic agents during angioplasty or stent delivery. The present invention satisfies these and other needs.

SUMMARY OF THE INVENTION

The invention is directed to an inflatable member for delivery of therapeutic agents to a desired site within a patient's body, in particular, balloons for use with balloon catheters and stent delivery systems; and balloon catheters and stent delivery systems including the same; and methods for making and using the same.

The inflatable member of the present invention includes proximal and distal sections and an intermediate section longitudinally disposed therebetween. The balloon has an outer layer defining an outer wall of the inflatable member and an inner layer extending along at least a portion of the longitudinal dimension of the outer layer and forming a fluid tight seal with the outer layer at the proximal and distal sections. The outer and inner layers define an outer chamber therebetween for housing the therapeutic agent. The outer layer, at the portion which in part defines the outer chamber, includes apertures for delivering the therapeutic agent onto or about the site, upon inflation of the balloon. The inner layer defines, at least in part, a balloon interior chamber configured for fluid communication with at least a portion an elongated member, such as an inflation lumen of a balloon catheter.

In another embodiment, the inner layer also includes inner apertures for delivering pressurized bio-compatible fluid to the outer chamber. In a preferred embodiment, the inner apertures are set off from the outer apertures to enhance the mixing of the therapeutic agents as they are being released from the outer apertures.

The therapeutic agent may be a viscous agent, as for example in the form of a solid, powder, or simply a viscous liquid; or a non-viscous liquid. The therapeutic agent can be housed in the outer chamber, or in the alternative applied onto an inner surface of the outer chamber for future release onto or about the site.

When the therapeutic agent is a liquid, either or both embodiments with or without the inner layer apertures, can be used.

In the embodiment having inner apertures in the inner layer, the liquid agent, preferably, is viscous, such that it will not flow back into the balloon interior chamber through the inner layer apertures. In the alternative or in combination with the viscous liquid, the material for constructing the inner layer is such that the liquid agent once in the outer chamber is not permeable through the inner layer apertures. Upon introduction of a pressurized bio-compatible fluid (e.g., saline) into the balloon interior chamber, the fluid enters the outer chamber, mixes with the agent and is released through the outer layer apertures.

Preferably, when a viscous agent (e.g., solid, powder, or viscous liquid) is used, the inner layer, includes the inner layer apertures, and the agent is delivered to the site as described above.

In the alternative, the agent may be non-viscous. As such, the agent is released from the outer layer apertures when inflation fluid is directed to the balloon interior chamber through shaft inflation lumen. As the balloon interior chamber expands, the inner layer applies pressure onto the agent within the outer chamber releasing the agent through the outer layer apertures.

BRIEF DESCRIPTION OF THE DRAWINGS

FIG. 6A is a partial longitudinal cross sectional view of the balloon of FIG. 1 formed of two parts, with one being insertable into another.

FIG. 6B is a partial longitudinal cross sectional view of the balloon parts of FIG. 6A brought together to form the balloon of FIG. 1.

DETAILED DESCRIPTION OF THE INVENTION

Figure 1:
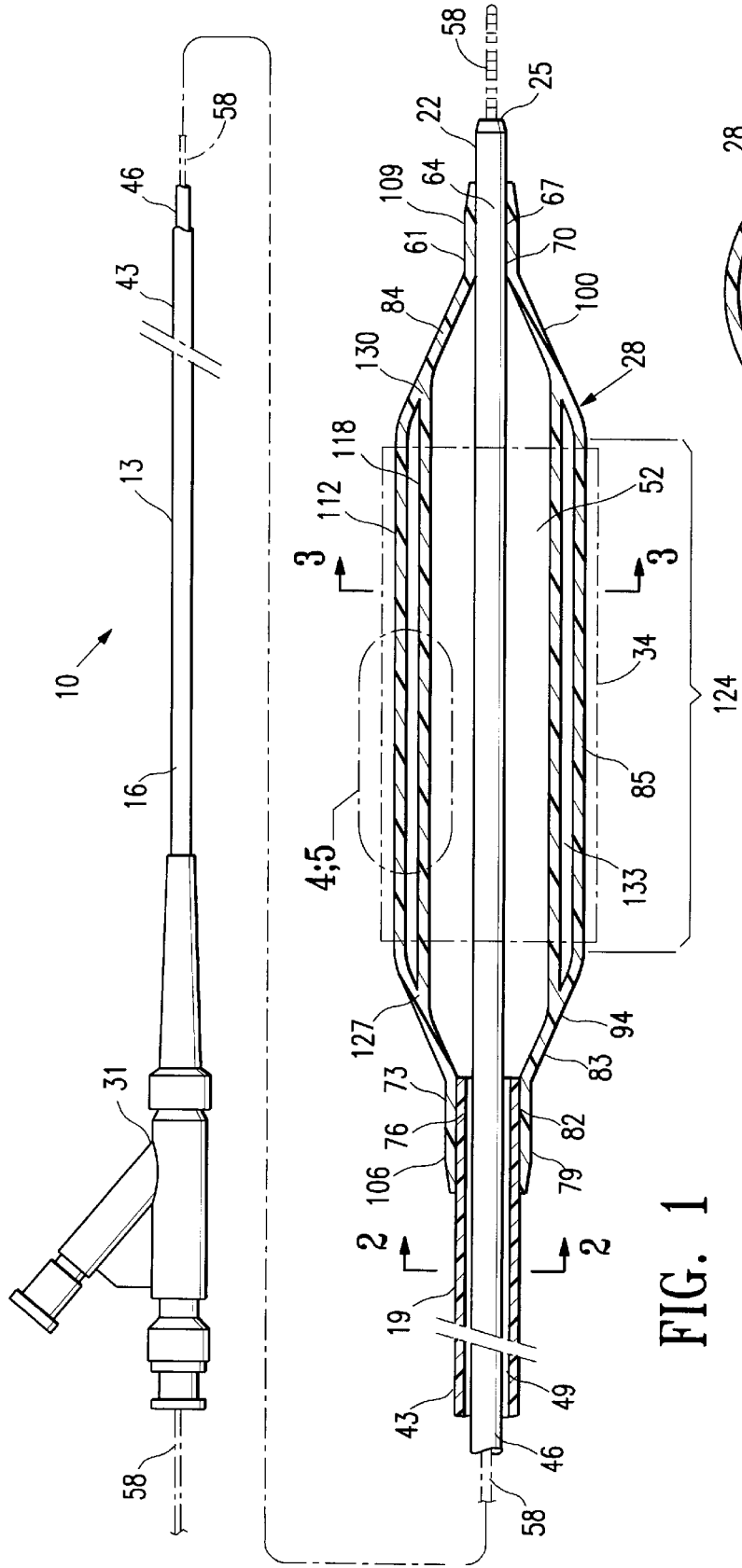
FIG. 1 is a longitudinal cross sectional view of a balloon catheter embodying features of the invention showing a double layered balloon configured to include a therapeutic agent between the two layers.

FIG. 1 illustrates a balloon catheter 10 embodying features of the invention, generally including, an elongated catheter shaft 13 having a proximal section 16 and a distal section 19 with a distal end 22 and a distal tip 25, an inflatable balloon 28 on the distal section 19 of the catheter shaft 13, and an adapter 31 mounted on the proximal section 16 of the catheter shaft 13. In FIG. 1, the catheter 10 is illustrated prior to expansion of the balloon 28.

Figure 2:
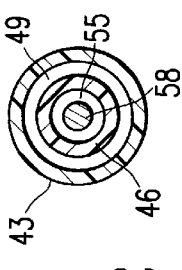
FIG. 2 is a transverse cross sectional view of the delivery system of FIG. 1 taken along line 2—2.
Figure 3:
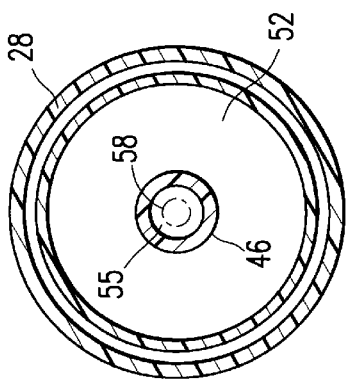
FIG. 3 is a transverse cross sectional view of the delivery system of FIG. 1 taken along line 3—3.

In the embodiment illustrated in FIG. 1, the catheter shaft 13 has an outer tubular member 43 and an inner tubular member 46 disposed within the outer tubular member 43 and defining, with the outer tubular member, an inflation lumen 49. The inflation lumen 49 is in fluid communication with an interior chamber 52 of the balloon 28. The inner tubular member 46 has an inner lumen 55 extending therein configured to slidably receive a guidewire 58 (shown in phantom) suitable for advancement through a patient's vasculature. A distal extremity 61 of the balloon 28 is sealingly secured to a distal extremity 64 of the inner tubular member 46 to form a distal seal 67 at distal junction 70 and a proximal extremity 73 of the balloon 28 is sealingly secured to a distal extremity 76 of the outer tubular member 43 to form a proximal seal 79 at a proximal junction 82. FIGS. 2 and 3 illustrate transverse cross sectional view of the catheter system 37 shown in FIG. 1, taken along lines 2—2 and 3—3, respectively.

Referring back to FIG. 1, the balloon 28 has proximal and distal sections, 83 and 84, and an intermediate section 85 located therebetween, preferably centrally, for receiving a stent 34 (shown in phantom) when the catheter 10 is used a stent delivery system, on all or a portion of the intermediate section 85. The proximal section 83 and distal section 84 of the balloon 28 include proximal and distal shoulder segments, 94 and 100, respectively, adjacent the intermediate section 85. The proximal and distal shoulder sections, 94 and 100, taper down in a direction away from the intermediate section 85, to proximal and distal shafts 106 and 109, respectively. The proximal and the distal balloon shafts, 106 and 109, are secured to the outer tubular member 43 and the inner tubular member 46, respectively, using a variety of suitable means such as adhesive and fusion bonding.

The balloon 28 includes an outer layer 112 defining an outer wall 115; and an inner layer 118 defining an inner wall 121 extending along at least a portion 124 of the outer layer 112, preferably, along the intermediate section 85, and defining at least in part the balloon interior chamber 52. The inner layer 118 forms proximal and distal fluid tight seals, 127 and 130, with the outer layer 112, at the proximal and distal sections, 83 and 84, respectively. The outer and inner layers, 112 and 118, define an outer chamber 133 therebetween for housing one or more therapeutic agents 136 to be delivered onto or about a specific site within the patient's body as the balloon 28 is inflated at or about the desired site within the patient's body.

Figure 4:
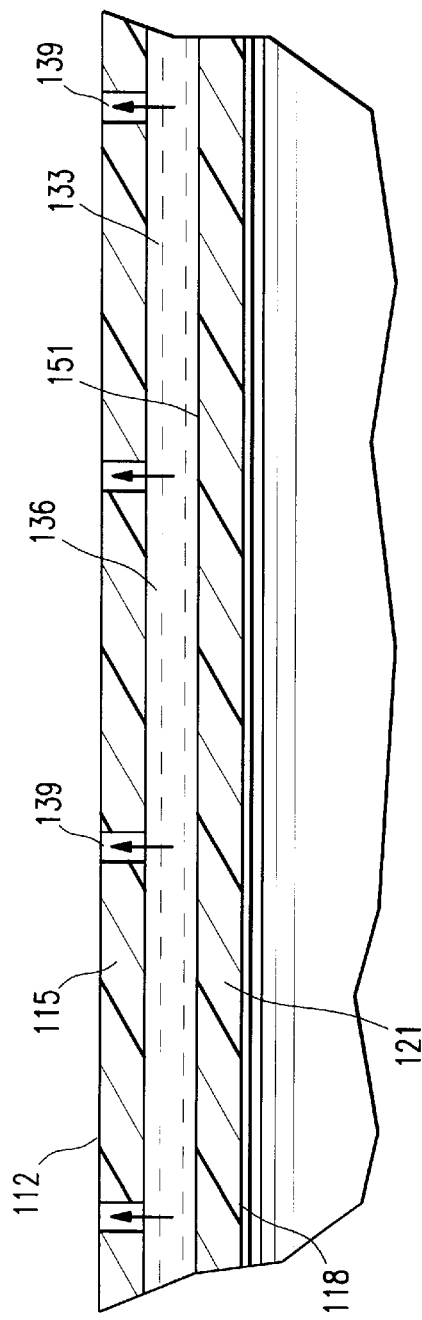
FIG. 4 is a partial longitudinal cross sectional view of the balloon of FIG. 1 showing an outer layer having perforations therein.
Figure 5:
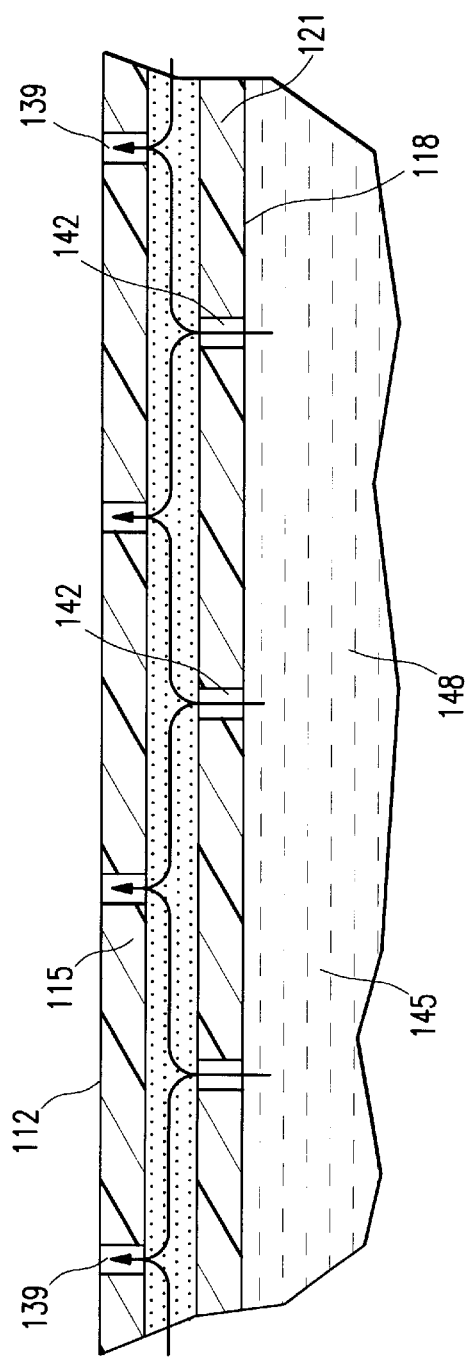
FIG. 5 is a partial longitudinal cross sectional view of an alternate embodiment of the balloon of FIG. 1 showing both layers having perforations therein.

As is best shown in FIGS. 4 and 5, the outer layer 112 includes one or more apertures 139 in the portion 124 of the outer chamber wall 112 which defines the outer chamber 133. The outer layer perforations 139 are used to deliver the therapeutic agent 136 onto or about the desired site.

In one embodiment, features of which are illustrated in FIG. 5, the inner layer 118, includes one or more apertures 142 in the inner wall 121. Preferably, the inner layer apertures 142 are set off from the outer layer apertures 139. The inner layer perforations 142 allow bio-compatible fluid 145 or other fluid therapeutic agents 148 introduced under pressure through the shaft inflation lumen 49 or other lumens extending within the shaft inflation lumen 49 (not shown) to pass through the inner layer 118 and into the outer chamber 133, for subsequent release onto or about the desired site.

The therapeutic agent 136 may be a viscous agent, as for example in the form of a solid, powder, or simply a viscous liquid; or a non-viscous liquid. The therapeutic agent 136 can be housed in the outer chamber 133, or in the alternative applied onto the inner surface 151 of the outer chamber 133 for future release onto or about the site.

Preferably, when the therapeutic agent is a liquid, either or both embodiments with or without the inner layer apertures 142, can be used.

When the inner layer 118 includes apertures 142, the liquid agent, preferably, is viscous, such that it will not flow back into the balloon interior chamber 55 through the inner layer apertures 142. In the alternative or in combination with the viscous liquid, the material for constructing the inner layer 118 is such that the liquid agent once in the outer chamber 133 is not permeable through the inner layer apertures 142. Upon introduction of the pressurized bio-compatible fluid 145 (e.g., saline) into the balloon interior chamber 55, the fluid 145 enters the outer chamber 133, mixes with the agent 136 and is released through the outer layer apertures 139.

Preferably, when a viscous agent (e.g., solid, powder, or viscous liquid) is used, the inner layer 118, includes the inner layer apertures 142, and the agent is delivered to the site as described above.

In the alternative, the agent 136 may be non-viscous. As such, the agent 136 is released from the outer layer apertures 139 when pressurized inflation fluid is directed to the balloon interior chamber 55 through shaft inflation lumen 49. As the balloon interior chamber 55 expands, the inner layer 118 applies pressure onto the agent 136 within the outer chamber 133 releasing the agent through the outer layer apertures 139.

The material for forming the balloon 28, including the outer and the inner layers, 112 and 118, includes any polymeric material conventionally used in the art. Preferably, the material includes: polyolefins, polyolefin copolymers and their blends; polyamides (e.g., Nylon 12), polyamide block copolymers (e.g., Pebax) and their blends (e.g., Nylon 12/Pebax and Pebax/Pebax blends); polyurethane block copolymers with MDI, HMDI or TDI hard segment and aliphatic polyester, polyether or polycarbonate soft segment (e.g., Pellethane, Estane or Bionate); polyester (e.g., PET) and polyester copolymers with 4GT (PBT) hard segment and aliphatic polyester or polyether soft segments (e.g., Hytrel, Pelprene or Arnitel).

Figure 7A:
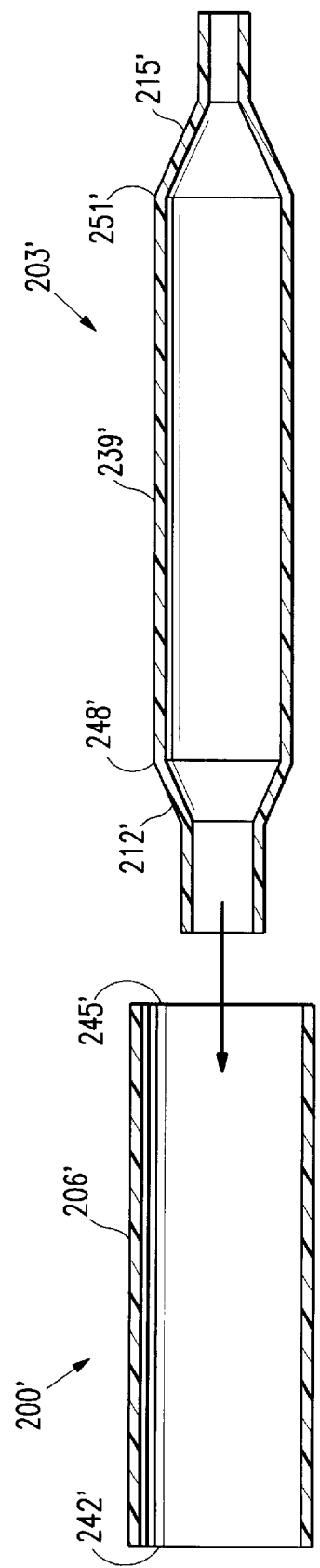
FIG. 7A is a partial longitudinal cross sectional view of an alternate embodiment of the balloon of FIG. 1 formed of two parts, with one being slidable over the other.
Figure 7B:
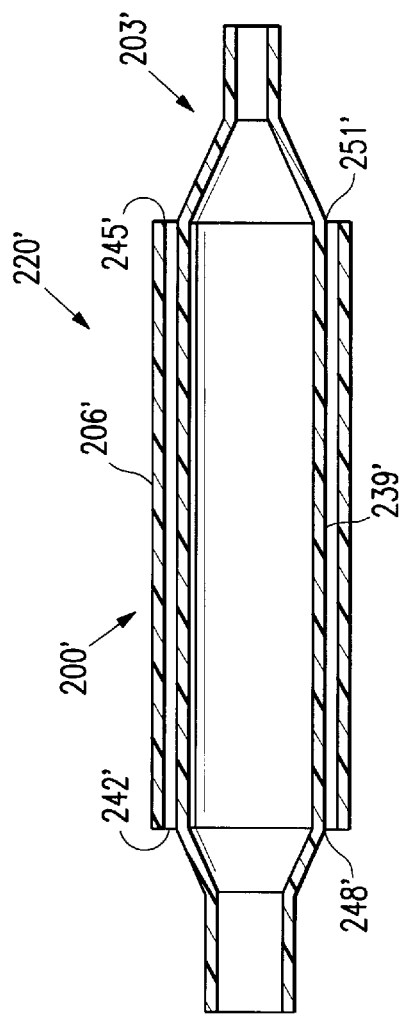
FIG. 7B is a partial longitudinal cross sectional view of the balloon parts of FIG. 7A brought together to form the balloon of FIG. 1.

The balloons of the present invention may be formed as illustrated in FIGS. 6 and 7.

As illustrated in FIG. 6, balloon 28 can be formed of two separate tubular segments, an outer and an inner segment, 200 and 203, for forming the outer and inner layers, 112 and 118, respectively. The outer and inner segments, 200 and 203, include outer and inner tubular sections, 206 and 209, having substantially similar lengths, and together for forming an the balloon intermediate section 85, with the inner segment 203 having a smaller nominal inner diameter than the outer segment 200. One of the outer and inner segments, 200 and 203, includes a proximal section 212 corresponding to the proximal section 83 of the balloon 28 while the other segment includes a distal section 215 corresponding to the distal section 84 of the balloon 28. In the embodiment illustrated in FIG. 6, the outer and inner segments, 200 and 203, include the proximal and distal sections, 212 and 215, respectively.

In forming an assembly 220, the inner segment 203 is inserted into the outer segment 200, until an end 223 of the inner segment 203 opposite the inner segment distal section 215 is lined up with a proximal end 226 of the outer segment 200, with the outer and inner tubular sections, 206 and 209, extending substantially parallel to one another forming an intermediate section 229. The assembly 220 is then sealed at the proximal and distal sections, forming the balloon 28, described above.

In another embodiment, as illustrated in FIG. 7, the outer segment 200' has a tubular section 206' corresponding to the balloon 28 intermediate section 85. The inner segment 203' is formed in the shape of the balloon 28, and includes, proximal and distal sections, 212' and 215', respectively, and an intermediate section 239' disposed therebetween. The inner segment 203' has a nominal inner diameter smaller than that of the outer 133 segment 200'. The outer tubular section 206' and the inner segment intermediate section 239' have substantially similar lengths, and together form the balloon intermediate section 85.

In forming an assembly 220', the inner segment 203 is inserted into the outer segment 200, until proximal and distal ends, 242' and 245', of the outer segment tubular section 206' are lined up with proximal and distal ends, 248' and 251' of the inner segment intermediate section 239', with the outer tubular section 206' and inner intermediate section 239' extending substantially parallel to one another. The assembly 220' is then sealed at the proximal and distal sections, forming the balloon 28 described above.

The therapeutic agent 136 is introduced into the outer chamber 133 (or the interior surface thereof) during one or more stages. By way of example, the agent 136 may be introduced into the outer chamber 133 before the outer and inner layers form the fluid tight seals, or it may be introduced after formation using an injection process (e.g., introducing a hypodermic needle containing the agent through the polymeric outer layer), or the agent, as for example when using a viscous liquid, may be applied onto the inner surface of the outer chamber 133 before the outer and inner layers are sealed at their ends.

While particular forms of the invention have been illustrated and described, it will be apparent that various modifications can be made without departing from the spirit and scope of the invention. Accordingly, it is not intended that the invention be limited, except as by the appended claims.

What is claimed is:

1. An inflatable member for delivery of therapeutic agents to a desired site within a patient's body and configured for use with an elongated tubular member, comprising:

proximal and distal sections and an intermediate section longitudinally disposed therebetween;

an outer layer defining an outer wall of the inflatable member;

an inner layer extending along at least a portion of the longitudinal dimension of the outer layer and forming a fluid tight seal with the outer layer at the proximal and distal section, the outer and inner layers defining an outer chamber therebetween with the outer layer having apertures in the outer chamber defining portion thereof, wherein the outer chamber includes at least one therapeutic agent to be released through the outer layer apertures upon the introduction of pressurized bio-compatible fluid through inner layer apertures; and an interior chamber defined at least in part by the inner layer and configured for fluid communication with at least a portion of the elongated member and wherein the inner layer includes said apertures therein.

2. The member of claim 1 wherein the therapeutic agent is viscous.

3. The member of claim 2 wherein upon the introduction of the pressurized bio-compatible fluid the viscous therapeutic agent becomes sufficiently mobile to pass through the outer layer apertures.

4. The member of claim 1 wherein the therapeutic agent is a solid.

5. The member of claim 1 wherein the therapeutic agent is a fluid.

6. A balloon catheter for delivery of therapeutic agents to a desired site within a patient's body, comprising:

an elongated shaft with proximal and distal shaft sections and an inflation lumen extending along at least a portion therein; and an inflatable member having a proximal and a distal section and an intermediate section longitudinally disposed therebetween, an outer layer defining an outer wall of the inflatable member, an inner layer extending along at least a portion of the longitudinal dimension of the outer layer and forming a fluid tight seal with the outer layer at the proximal and distal sections, the outer and inner layers defining an outer chamber therebetween with the outer layer and inner layer having apertures in the outer chamber defining portion thereof, and an interior chamber defined at least in part by the inner layer and in fluid communication with at least a portion of the elongated member inflation lumen, wherein the outer chamber includes at least one therapeutic agent to be released through the outer layer apertures upon the introduction of pressurized bio-compatible fluid through the inflation lumen and through the inner layer apertures.

7. The catheter of claim 6 wherein the therapeutic agent is viscous.

8. The catheter of claim 7 wherein upon the introduction of the pressurized bio-compatible fluid the viscous therapeutic agent becomes sufficiently mobile to pass through the outer layer apertures.

9. The catheter of claim 6 wherein the therapeutic agent is a solid.

10. The catheter of claim 6 wherein the therapeutic agent is a fluid.

11. An inflatable member for delivery of therapeutic agents to a desired site within a patient's body and configured for use with an elongated tubular member, comprising:

proximal and distal sections and an intermediate section longitudinally disposed therebetween;

an outer layer defining an outer wall of the inflatable member configured for supporting a deployable prosthetic device thereon;

an inner layer extending along at least a portion of the longitudinal dimension of the outer layer and forming a fluid tight seal with the outer layer at the proximal and distal section, the outer and inner layers defining an outer chamber therebetween with the outer layer having apertures in the outer chamber defining portion thereof, wherein the outer chamber includes at least one therapeutic agent to be released through the outer layer apertures upon the inflation of the inflatable member and wherein the inner layer includes apertures therein; and an interior chamber defined at least in part by the inner layer and configured for fluid communication with at least a portion of the elongated member.

12. A method for delivering a therapeutic agent onto or about a desired tissue site within a patient's body, comprising:

providing a catheter according to claim 6;

introducing a bio-compatible inflation fluid through the shaft inflation lumen into the balloon interior chamber;

forcing the bio-compatible fluid through the inner layer chamber and into the outer chamber;

pressurizing the balloon interior chamber; and ejecting the therapeutic agent out of the outer chamber apertures and onto or about the desired tissue site.

\* \* \* \* \*